(12) United States Patent
Ouchi

(10) Patent No.: US 7,766,908 B2
(45) Date of Patent: Aug. 3, 2010

(54) HIGH-FREQUENCY TREATING INSTRUMENT FOR ENDOSCOPE

(75) Inventor: Teruo Ouchi, Saitama (JP)

(73) Assignee: Hoya Coporation, Tokyo (JP)

( * ) Notice: Subject to any disclaimer, the term of this patent is extended or adjusted under 35 U.S.C. 154(b) by 1323 days.

(21) Appl. No.: 11/085,512

(22) Filed: Mar. 22, 2005

(65) Prior Publication Data

US 2005/0222567 A1    Oct. 6, 2005

(30) Foreign Application Priority Data

Mar. 31, 2004  (JP) ............ P2004-103982
May 21, 2004  (JP) ............ P2004-151269

(51) Int. Cl.
    *A61B 18/18*    (2006.01)
(52) U.S. Cl. .......................... 606/46; 606/41
(58) Field of Classification Search ............ 606/45–50, 606/41
    See application file for complete search history.

(56) References Cited

U.S. PATENT DOCUMENTS

| 5,261,905 | A | * | 11/1993 | Doresey, III ............ 606/45 |
| 5,300,069 | A | * | 4/1994 | Hunsberger et al. .......... 606/37 |
| 5,401,274 | A |  | 3/1995 | Kusunoki |
| 5,628,760 | A |  | 5/1997 | Knoepfler |
| 6,059,782 | A |  | 5/2000 | Novak et al. |
| 6,428,503 | B1 | * | 8/2002 | Kierce ............ 604/43 |
| 6,802,842 | B2 | * | 10/2004 | Ellman et al. ............ 606/45 |

FOREIGN PATENT DOCUMENTS

| JP | 5-293115 | 11/1993 |
| JP | 5-93411 | 12/1993 |
| JP | 6-292685 | 10/1994 |
| JP | 2001-57984 | 3/2001 |
| JP | 2002-153484 | 5/2002 |

OTHER PUBLICATIONS

English language Abstract of JP 2001-57984, Mar. 6, 2001.
English Language Abstract of JP 2002-153484, (2002).
English Language Abstract of JP 6-292685, (2002).
U.S. Appl. No. 11/086,436, filed Mar. 23, 2005, Ouchi.

* cited by examiner

*Primary Examiner*—Michael Peffley
(74) *Attorney, Agent, or Firm*—Greenblum & Bernstein, P.L.C.

(57) ABSTRACT

A high-frequency treating instrument for an endoscope, includes: a spatula-form high-frequency electrode which is adapted to be protruded from and housed within an insulated flexible sheath of the endoscope; and a concavo-convex portion which serves as an antiskid member when the concavo-convex portion is brought into contact with a mucous membrane and is formed on at least one of side edge portions of a portion closer to a tip end of the high-frequency electrode.

4 Claims, 11 Drawing Sheets

HIGH-FREQUENCY TREATING INSTRUMENT FOR ENDOSCOPE

BACKGROUND OF THE INVENTION

The present invention relates to a high-frequency treating instrument for an endoscope which is passed through the treating instrument insertion channel of the endoscope so as to perform a transendoscopic mucous membrane exfoliation operation etc.

In the case of performing a transendoscopic mucous membrane exfoliation operation, in general, physiological saline solution etc. is injected under a mucous membrane to be exfoliated to raise the mucous membrane, and the periphery of the raised portion is resected by a high-frequency treating instrument etc. for an endoscope which tip end portion is bent in a hook shape (see patent documents 1, 2 and 3, for example).

Patent Document 1: JP-A-2002-153484

Patent Document 2: JP-A-6-292685

Patent Document 3: JP-A-5-293115

In the aforesaid related high-frequency treating instrument for an endoscope, although it is possible to resect the raised mucous membrane portion in a manner of surrounding the portion, it is difficult to exfoliate the raised mucous membrane portion from the tissue under the portion. Thus, it is required to withdraw the treating instrument for the resecting operation from the treating instrument insertion channel of the endoscope after the resecting operation, then an exfoliation instrument etc. for the endoscope of a spatula shape is inserted into the resected portion in place of the treating instrument for the resecting operation to exfoliate the mucous membrane portion from a sinew layer under the mucous membrane portion. Thus, since the exfoliation operation is complicated, such an operation is heavy burden for an operator and a patient.

Thus, in order so that both the mucous membrane resecting operation using a high-frequency current and the mucous membrane exfoliation operation succeeding thereto are performed by using a single treating instrument, it is considered to form a high-frequency electrode in a spatula shape such as a rice scoop.

However, when the high-frequency treating instrument is simply formed in the spatula shape such as a rice scoop, a mechanical hooking force thereof with respect to a mucous membrane is small. Thus, at the time of the mucous membrane resecting operation, when the high-frequency electrode is moved within a mucous membrane while it is cut into the mucous membrane, there may arise a case that the high-frequency electrode slides with respect to the mucous membrane and so rises above the surface of the mucous membrane, whereby the mucous membrane can not be resected smoothly.

SUMMARY OF THE INVENTION

Accordingly, an object of the invention is to provide a high-frequency treating instrument for an endoscope which can perform both a mucous membrane resecting operation using a high-frequency electrode of a spatula shape and a mucous membrane exfoliation operation succeeding thereto by using a single treating instrument, and further can perform a resecting operation smoothly at the time of the mucous membrane resecting operation in a manner that the treating instrument well bites to the mucous membrane surface to prevent the treating instrument from rising above the surface of the mucous membrane.

In order to solve the aforesaid object, the invention is characterized by having the following arrangement.

(1) A high-frequency treating instrument for an endoscope, comprising:

a spatula-form high-frequency electrode which is adapted to be protruded from and housed within an insulated flexible sheath of the endoscope; and a concavo-convex portion which serves as an antiskid member when the concavo-convex portion is brought into contact with a mucous membrane and is formed on at least one of side edge portions of a portion closer to a tip end of the high-frequency electrode.

(2) The high-frequency treating instrument according to (1), wherein the high-frequency electrode is coupled to an operating wire with electric conductivity which is disposed so as to freely move reciprocally in an axial direction within the flexible sheath.

(3) The high-frequency treating instrument according to (1), wherein each of tip ends of the concavo-convex portion has an almost square shape.

(4) The high-frequency treating instrument according to (1), wherein the side edge portion is formed at a portion closer to the tip end of the high-frequency electrode so as to be obliquely backward, and the concavo-convex portion is formed at the obliquely backward side edge portion.

(5) A high frequency incision piece for an endoscope, comprising:

a conductive rod which is adapted to be protruded from and housed within an insulated flexible sheath of the endoscope;

a high frequency incision piece which is formed at an end of the conductive rod, has a size capable of being housed in the sheath, and includes a flat plate portion deviated to one side from an extended line of a center axis line of the sheath, and a hook-shaped portion projecting from a front end portion of the flat plate portion in a side direction to be deviated in a direction opposed to the flat plate portion from the extended line of the center axis line.

(6) The high frequency incision piece according to (5), wherein a conductive operating wire is arranged to insert into the sheath extractably and retractably in the axis line direction and the conductive rod is connected to a front end portion of the operating wire.

(7) The high frequency incision piece according to (5) wherein a root portion of the hook-shaped portion is widened as compared with an end portion of the hook-shaped portion.

(8) The high frequency incision piece according to (5), wherein the hook-shaped portion is formed with a concavo-convex portion which serves as an antiskid member when the concavo-convex portion is brought into contact with a mucous membrane.

(9) A high frequency incision piece for an endoscope, comprising:

a conductive rod which is adapted to be protruded from and housed within an insulated flexible sheath of the endoscope; and a high frequency incision piece which is formed at an end of the conductive rod, has a size capable of being housed in the sheath, and has an asymmetrical shape across an extended line of a center axis line of the sheath.

DETAILED DESCRIPTION OF PREFERRED EMBODIMENTS

First Embodiment

A first embodiment according to the invention will be described with reference to the accompanying drawings.

Figure 1:
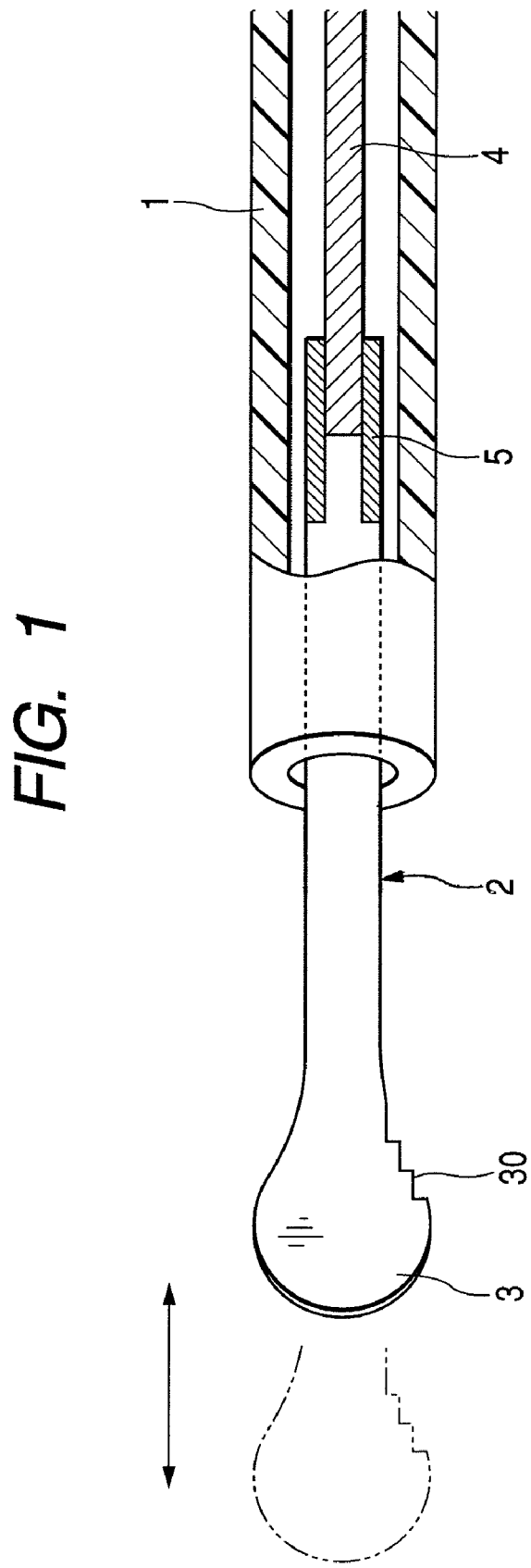
FIG. 1 is a sectional diagram showing the side portion of the tip end of a high-frequency treating instrument for an endoscope according to a first embodiment of the invention.

FIG. 1 shows the tip end of a high-frequency treating instrument for an endoscope according to the first embodiment, which is arranged in a manner that an operating wire 4 with electric conductivity is inserted entirely so as to freely move reciprocally in the axial direction within a flexible sheath 1 which is configured by a flexible tube with electric insulation properties such as a tetrafluoroethylene resin tube.

A high-frequency electrode 2 formed by a flat stainless steel plate, for example, is provided at the tip end of the operating wire 4 via a coupling pipe 5 made of stainless steel pipe member etc. in a manner that the electrode is disposed at the tip end of the flexible sheath 1 so as to be freely protruded from and housed within the tip end of the flexible sheath 1.

A portion of the high-frequency electrode 2 closer to the tip end thereof is widened so as to be configured in a spatula shape such as a rice scoop. A concavo-convex portion 30 is formed at the obliquely backward portion of the side edge portion of the widened portion 3.

The concavo-convex portion 30 is configured in a notched shape such that each of tip ends thereof has an almost square shape with an angle of about 90 degrees. Thus, the concavo-convex portion serves as an antiskid member for preventing the widened portion from sliding with respect to a mucous membrane when the concavo-convex portion is brought into contact with the mucous membrane of a living body. In this first embodiment, although the concavo-convex portion 30 is provided only at the one side edge portion of the widened portion 3 of the high-frequency electrode 2, the concavo-convex portion 30 may also be provided at the obliquely backward portion of the other side edge portion of the widened portion which is on the opposite side of the one side edge portion.

An operation portion for reciprocally moving the operating wire 4 is coupled on the not-shown base end side of the flexible sheath 1 so that the high-frequency electrode 2 is freely protruded from and housed within the tip end of the flexible sheath 1 through the remote operation of the operation portion. Further, a high-frequency current can be arbitrarily supplied to the high-frequency electrode 2 through the operating wire 4 from the operation portion side.

Figure 2:
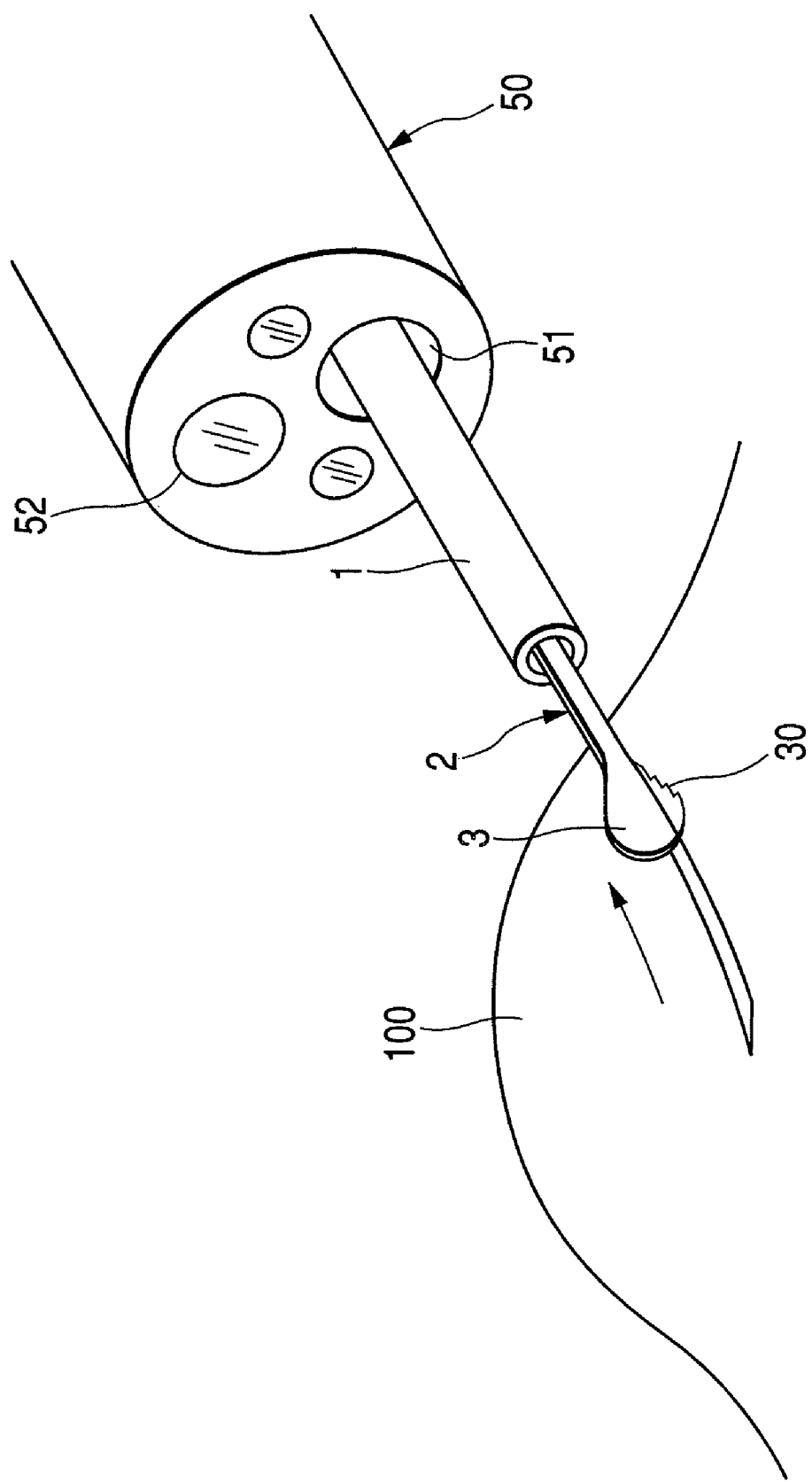
FIG. 2 is a schematic diagram showing a state where a mucous membrane is resected by using the high-frequency treating instrument for an endoscope according to the first embodiment of the invention.

FIG. 2 shows a state where a mucous membrane 100 is resected by using the high-frequency treating instrument for an endoscope according to the first embodiment configured in the aforesaid manner, in which the tip end of the flexible sheath 1 is protruded from the treatment instrument insertion channel 51 of the endoscope 50 and positioned within an observation range from an observation window 52.

Then, the widened portion 3 of the high-frequency electrode 2 is abutted against the surface of the mucous membrane 100 in a standing state. Thereafter, the high-frequency current is supplied to the electrode and then the high-frequency electrode 2 is pulled toward the flexible sheath 1 side, whereby the mucous membrane 100 is resected at the contact portion between the high-frequency electrode 2 and the widened portion 3.

In this case, since the concavo-convex portion 30 formed at the side edge portion of the widened portion 3 of the high-frequency electrode 2 cuts and opens the mucous membrane 100 while cauterizing the mucous membrane in a state that the concavo-convex portion bites the mucous membrane 100, the mucous membrane 100 can be resected smoothly without causing such a phenomenon that the widened portion slides with respect to the mucous membrane and so rises above the surface of the mucous membrane.

Figure 3:
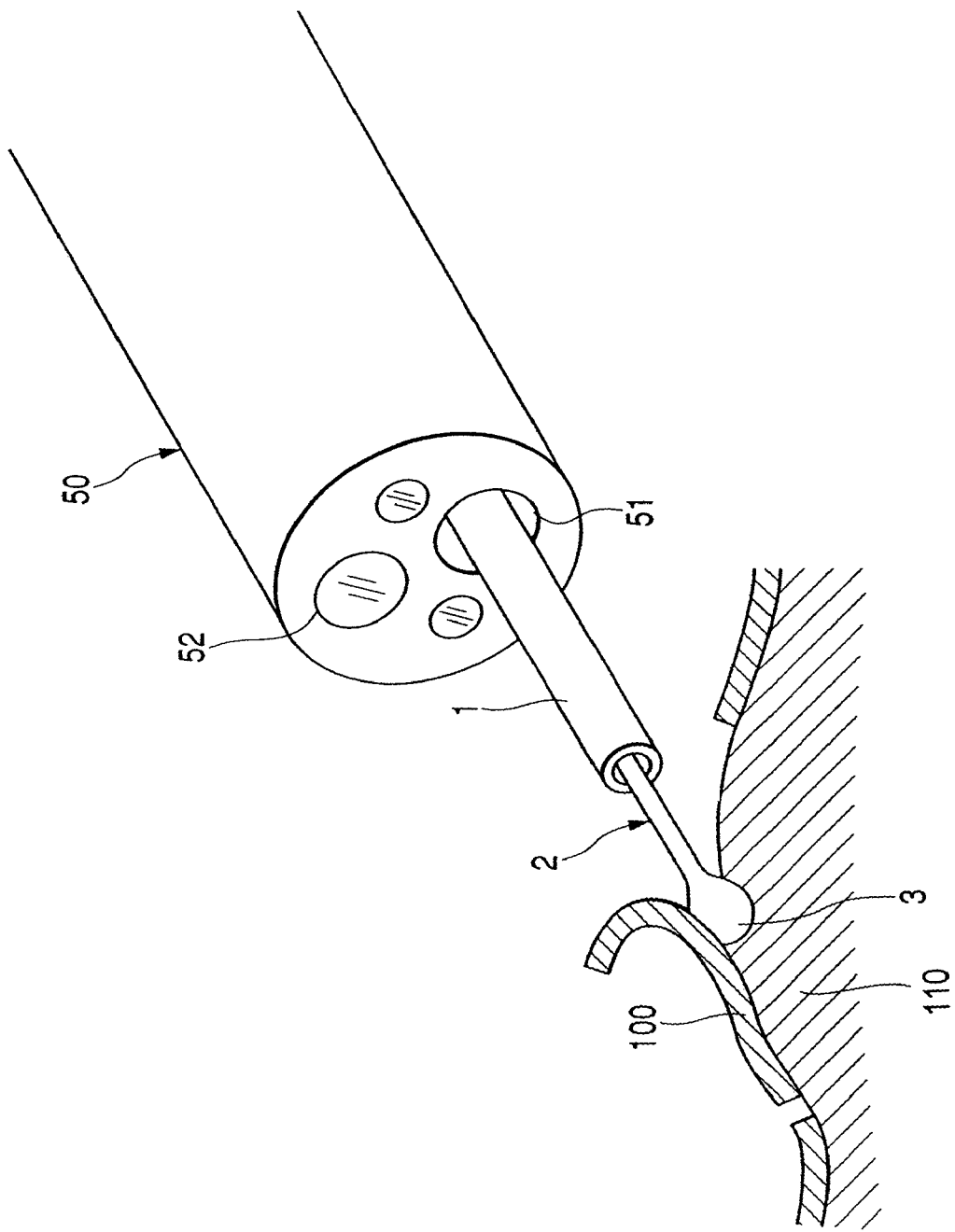
FIG. 3 is a schematic diagram showing a state where a mucous membrane is resected by using the high-frequency treating instrument for an endoscope according to the first embodiment of the invention.

After the mucous membrane 100 is resected in a circular shape so as to surround the portion to be resected, the high-frequency electrode 2 is laid horizontally as shown in FIG. 3. Then, the widened portion 3 is inserted into the resected portion of the mucous membrane 100 without supplying the current to the electrode and is moved upward.

According to such an operation, the mucous membrane 100 at the inside of the resected portion can be exfoliated from a sinew layer 110 under the mucous membrane. Further, since the high-frequency electrode 2 is configured in a flat plate shape, the exfoliation operation can be performed easily and surely.

Second Embodiment

Figure 4:
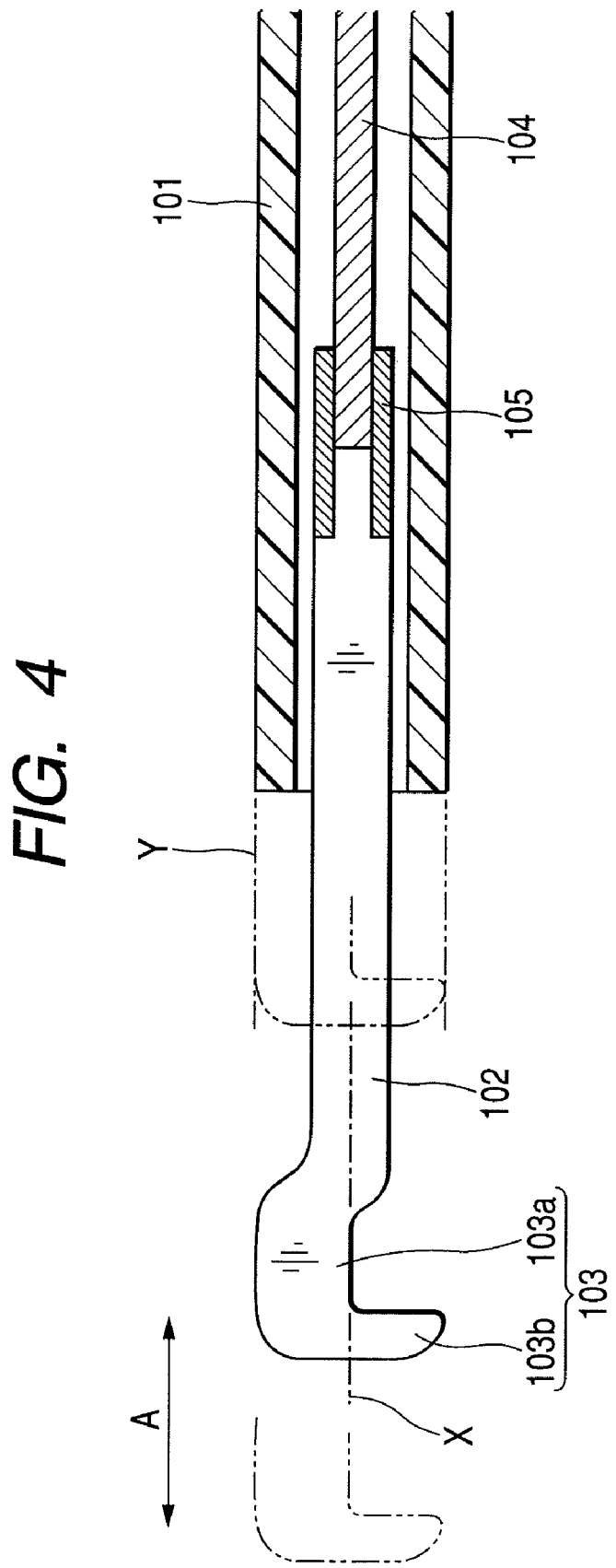
FIG. 4 is a side sectional view of a front end portion of a high frequency incision piece for an endoscope according to a second embodiment of the invention.
Figure 5:
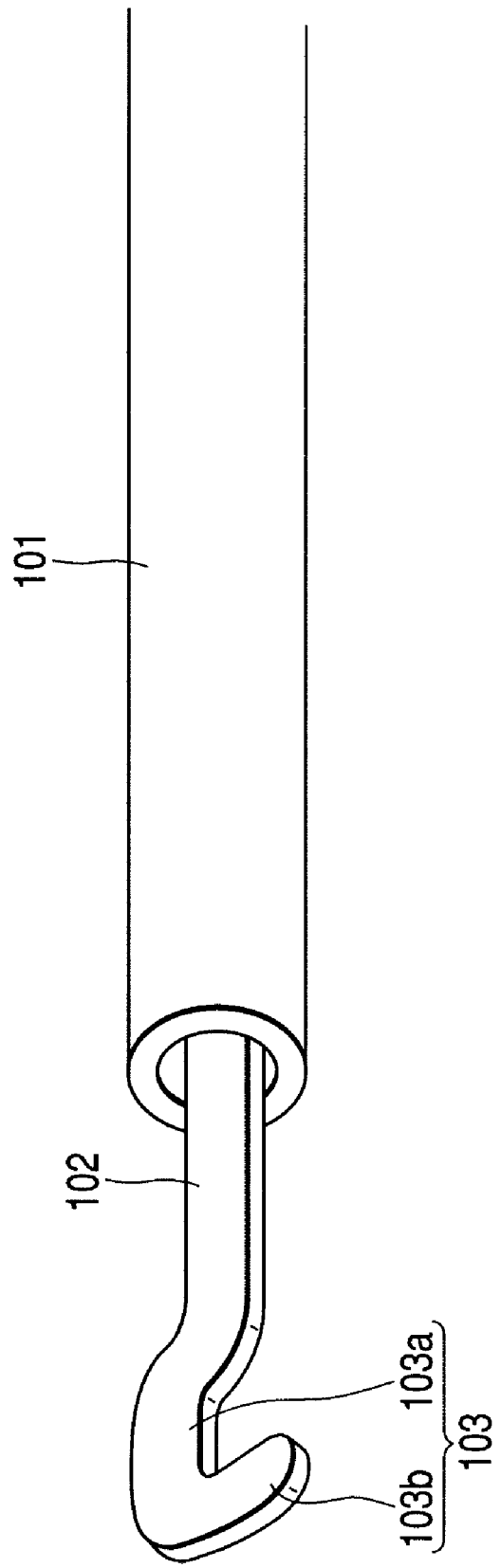
FIG. 5 is a perspective view of the front end portion of the high frequency incision piece for an endoscope according to the second embodiment of the invention.

FIG. 5 is a perspective view of a front end portion of a high frequency incision piece for an endoscope according to a second embodiment FIG. 4 is a side sectional view thereof, and a conductive operating wire 104 is arranged to insert into a sheath 101 comprising an electrically insulating flexible tube of, for example, an ethylene tetrafluoride tube or the like extractably and retractably in an axis line direction over a total length thereof.

At a front end of the operating wire 104, a conductive rod 102 formed by, for example, a stainless steel sheet or the like is arranged at a front end portion of the sheath 101 to be able to be protruded from and housed within the front end of the sheath 101 via a connecting pipe 105 comprising a stainless steel pipe member or the like, and a high frequency electrode 103 is formed at a front most portion of the conductive rod 102.

The high frequency electrode 103 of the second embodiment is formed by pressing and punching the stainless steel sheet integrally with the conductive rod 102 and is formed by a constant wall thickness as a whole. However, the high frequency electrode 103 and the conductive rod 102 may be formed by connecting a separate member thereto.

The high frequency electrode 103 is formed by a flat plate portion 103a continuous to the conductive rod 102 and a hook-shaped portion 103b formed to project from a front end portion of the flat plate portion 103a in a side direction, the flat plate portion 103a is formed on a side deviated to one side from an extended line X of a center axis line of a front end portion of the sheath 101 and the hook-shaped portion 103b is formed to deviate in a direction opposed to the flat plate portion 103a from the extended line X of the center axis line of the front end portion of the sheath 101.

Further, the high frequency electrode 103 is disposed in a range which is not projected outward from an extended face Y of an outer edge of the front end portion of the sheath 101 and the hook-shaped portion 103b is disposed on a plane the same as that of the flat plate portion 103a. By such an arrangement, the flat plate portion 103a and the hook-shaped portion 103b are ensured with sizes which are necessary sufficient for respectively carrying out effective treatments although the sizes are sizes by which the high frequency electrode 103 does not jump out from the front end to the side of the sheath 101.

A base end side of the sheath 101, not illustrated, is connected with an operating portion for operating to extract and retract the operating wire 104, the conductive rod 102 can be inserted into and from the front end of the sheath 101 by remote operation from the operating portion, and a high frequency current can arbitrarily be conducted from the side of the operating portion to the high frequency electrode 103 via the operating wire 104 and the conductive rod 102.

As shown by an arrow mark A in FIG. 4, the high frequency electrode 103 can be extracted and retracted in the axis line direction of the front end portion of the sheath 101 in accordance with extraction and retraction of the conductive rod 102 and is larger than an inner diameter dimension of the sheath 101 and therefore, the high frequency electrode 103 is not brought into a state of being drawn into the sheath 101.

Further, in inserting the high frequency incision piece for the endoscope of the second embodiment through the treatment piece inserting channel of the end scope, when the high frequency electrode 103 is brought into a state of being brought into contact with a position of a front end opening to the sheath 101, the high frequency electrode 103 is disposed within a range of not projected outward from the extended face Y of the outer edge of the front end portion of the sheath 101 and therefore, the high frequency incision piece can be inserted and detached safely and smoothly without being caught by inside of the treatment piece inserting channel and without being destructed.

Figure 6:
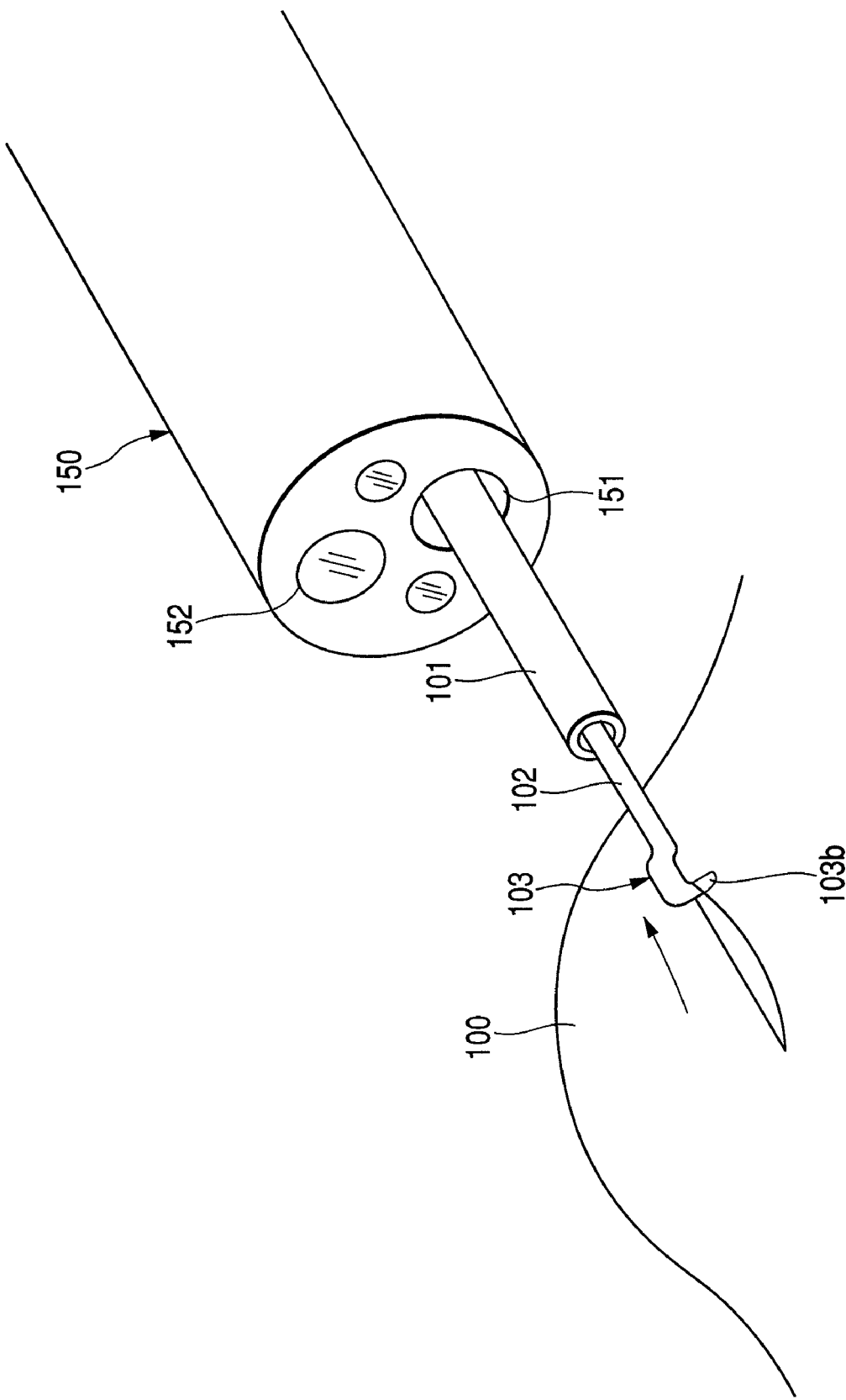
FIG. 6 is an outline view of a state of incising the mucosa by the high frequency incision piece for an endoscope according to the second embodiment of the invention.

FIG. 6 shows a state of incising the mucosa 100 by using the high frequency incision piece for the endoscope according to the second embodiment constituted as described above and the front end portion of the sheath 101 is projected from a treatment piece inserting channel 151 of an endoscope 150 to be disposed within an observing range from an observing window 152.

Further, by attaching the hook-shaped portion 103b of the high frequency electrode 103 to a surface of the mucosa 100 in a state of being erected relative thereto, conducting a high frequency current and pulling the conductive rod 102 to a side of the sheath 101, the mucosa 100 is burnt at a portion thereof brought into contact with the hook-shaped portion 103b and is incised along a range of moving the hook-shaped portion 103b.

Figure 7:
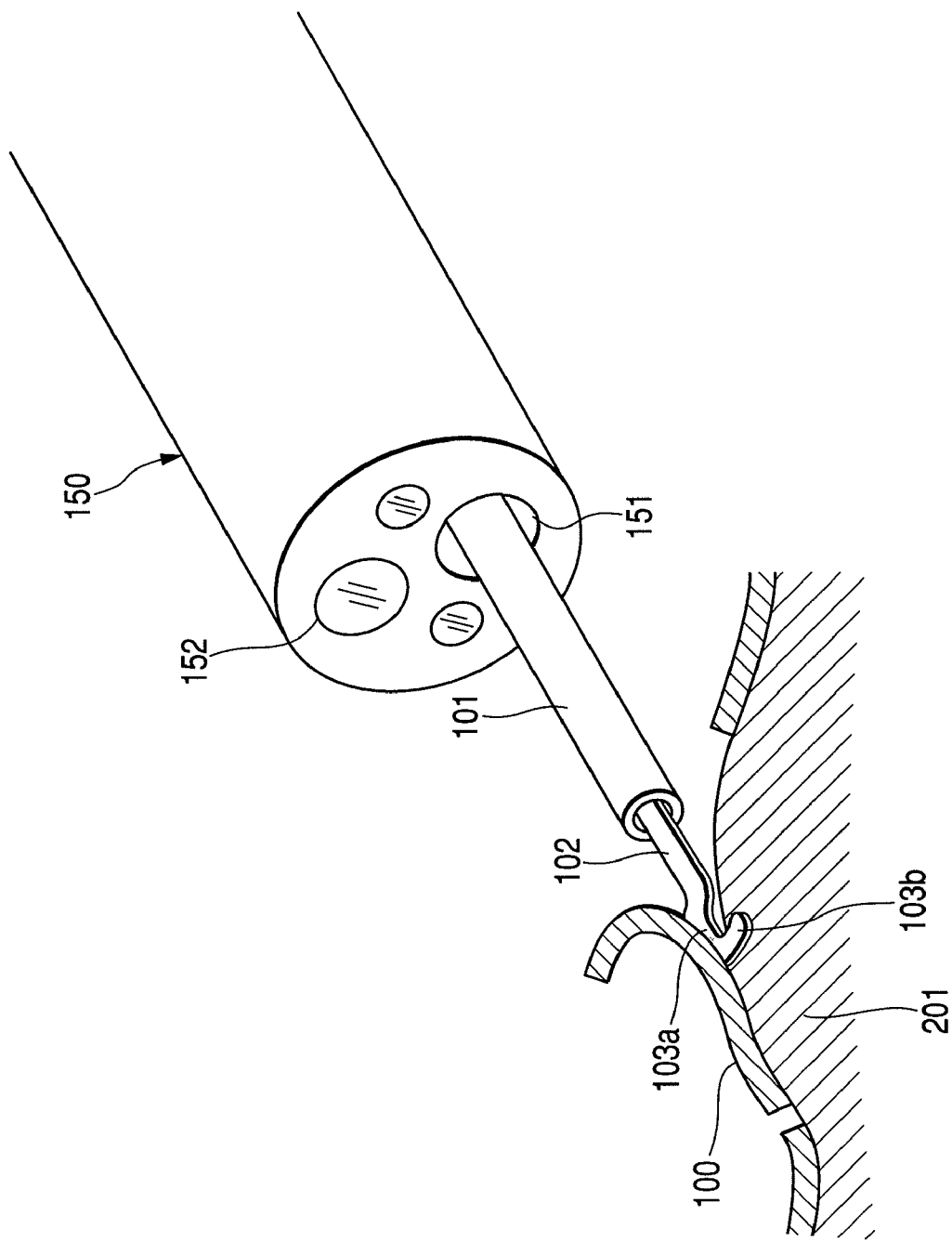
FIG. 7 is an outline view of a state of ablating the mucosa by the high frequency incision piece for an endoscope according to the second embodiment of the invention.

When the mucosa 100 is incised in a ring-like shape to surround a portion of an object to be ablated, as shown by FIG. 7, by making the high frequency electrode 103 horizontal and inserting the flat plate portion 103a into the incised portion of the mucosa 100 to scoop up without conducting the high frequency current, the mucosa 100 of the portion surrounded by the incised portion can be ablated from the muscle layer 201 or the like therebelow.

Figure 8:
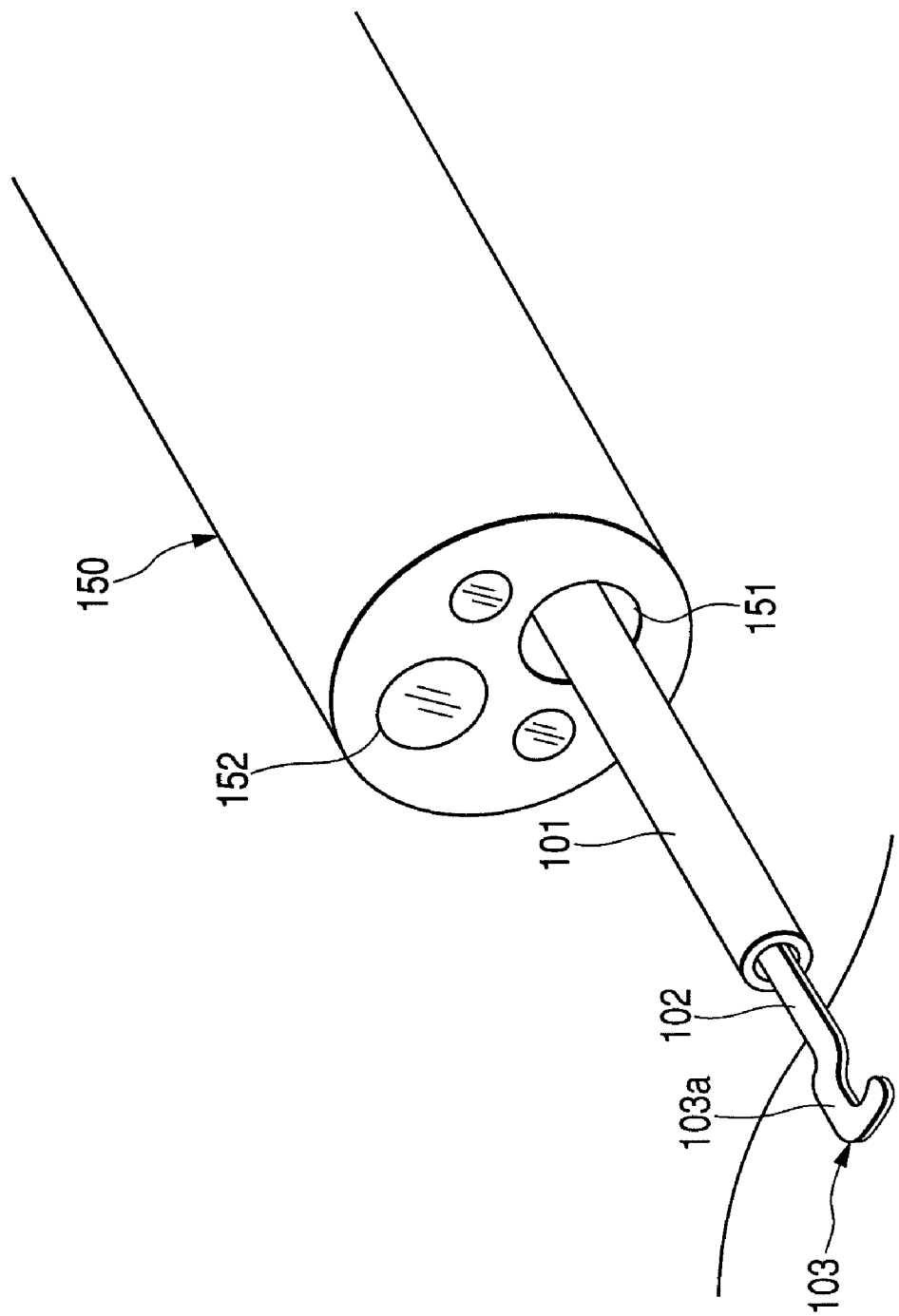
FIG. 8 is an outline view of a state of carrying out hemostasis by the high frequency incision piece for an endoscope according to the second embodiment of the invention.

Further, when the hemorrhage is brought about by cutting the blood vessel at the ablated portion, as shown by FIG. 8, by pressing a plane portion of the flat plate portion 103a to the bleeding portion to be brought into face contact therewith while conducting the high frequency current to the high frequency electrode 103, the bleeding portion and a surrounding thereof are burnt and coagulated by the high frequency current having a low density and the hemostasis can easily be carried out.

Figure 9:
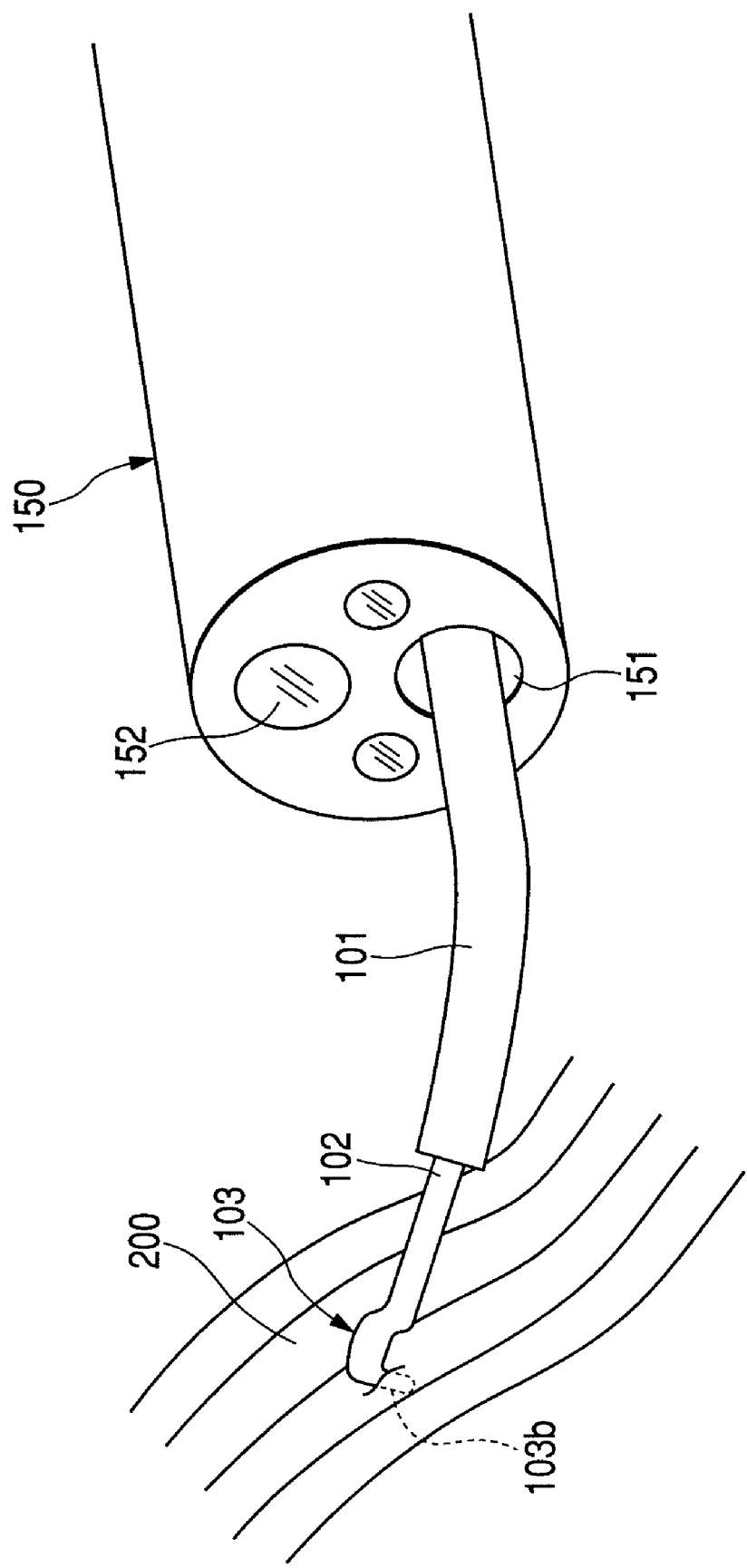
FIG. 9 is an outline view of a state of incising the muscular fiber tissue by the high frequency incision piece for an endoscope according to the second embodiment of the invention.

Further, as shown by FIG. 9, by inserting the hook-shaped portion 103b of the high frequency electrode 103 into the muscular fiber tissue 200 and pulling the conductive rod 102 to the side of the sheath 101 while conducting the high frequency current, also the muscular fiber tissue or the like can easily be incised.

Third Embodiment

Figure 10:
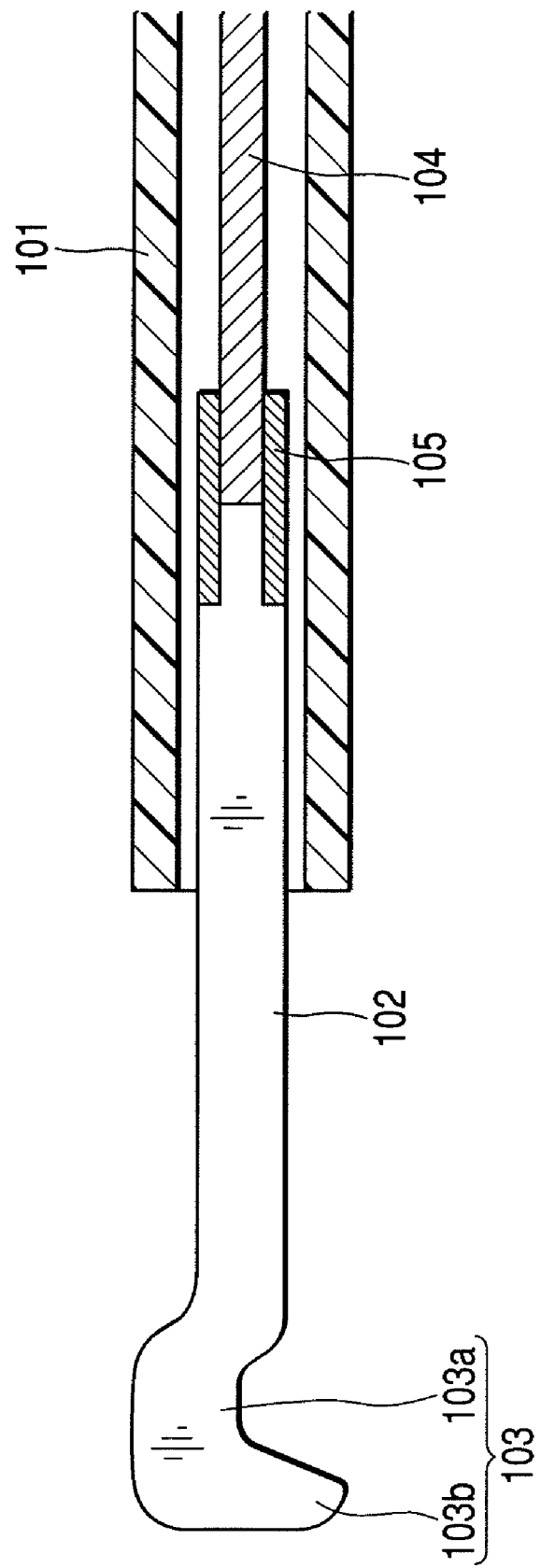
FIG. 10 is a side sectional view of a front end portion of a high frequency incision piece for an endoscope according to a third embodiment of the invention.

FIG. 10 shows a front end portion of a high frequency incision piece for an endoscope according to a third embodiment of the invention, and by widening a width of a root portion of the hook-shaped portion 103b, the hook-shaped portion 103b is formed to include a plane portion equivalent to that of the flat plate portion 103a. By constituting in this way, the hook-shaped portion 103b can effectively utilized in ablation and hemostasis along with the flat plate portion 103a.

Fourth Embodiment

Figure 11:
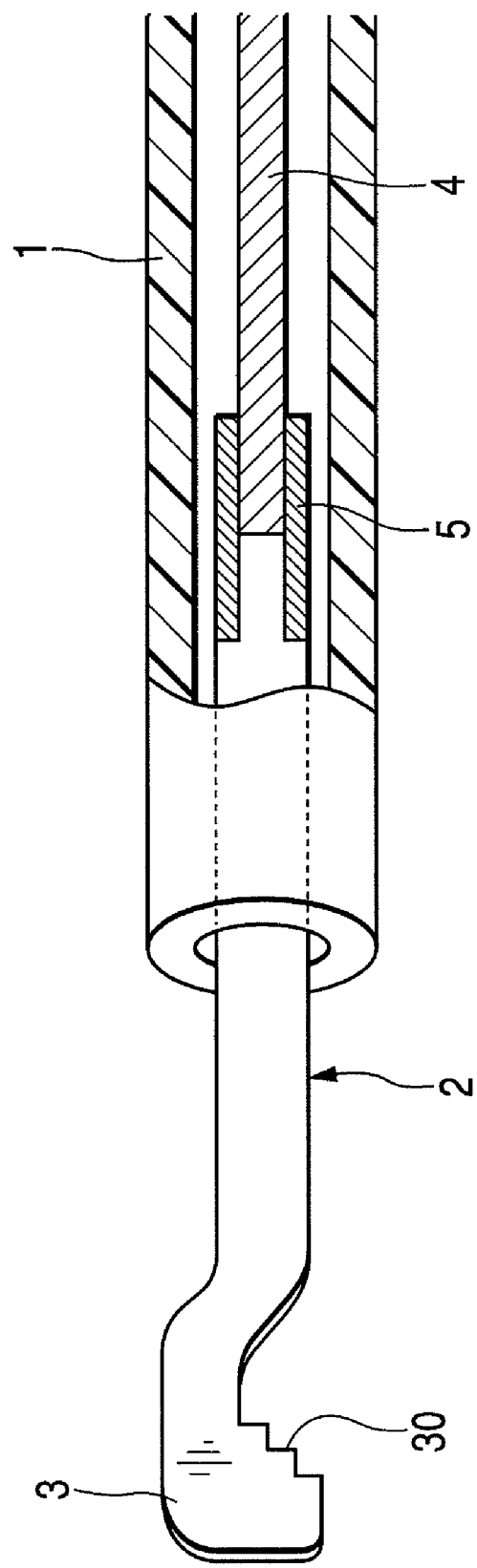
FIG. 11 is a sectional diagram showing the side portion of the tip end of a high-frequency treating instrument for an endoscope according to a fourth embodiment of the invention.

FIG. 11 shows a sectional diagram showing the side portion of the tip end of a high-frequency treating instrument for an endoscope according to a fourth embodiment of the invention. According to the fourth embodiment, a distal end of a conductive rod 2 has a shape of the high-frequency electrode according to the second embodiment and is formed with the concavo-convex portion 30 at an obliquely backward portion of a side edge portion as shown in FIG. 11.

Even when the high-frequency treating instrument is configured in this manner, like the first embodiment, the mucous membrane resecting operation can be performed smoothly without raising the widened portion above the surface of the mucous membrane 100 and the mucous membrane exfoliation operation can be performed succeedingly.

What is claimed is:
1. A high-frequency treating instrument for an endoscope, comprising:

a high-frequency electrode which is adapted to be protruded from and housed within an insulated flexible sheath of the endoscope, the high-frequency electrode having a proximal end and a generally teardrop—shaped distal tip end wider than said proximal end, said distal tip end further having side edge portions on a proximal side of said distal tip end; and a concavo-convex portion which serves as an antiskid member when the concavo-convex portion is brought into contact with a mucous membrane and is formed on at least one of said side edge portions, wherein the concavo-convex portion includes serrated tip ends, each tip end being generally square.

2. The high-frequency treating instrument according to claim 1, wherein the high-frequency electrode is coupled to an operating wire with electric conductivity, wherein the operating wire is disposed so as to freely move reciprocally in an axial direction within the flexible sheath.

3. The high-frequency treating instrument according to claim 1, wherein one of the side edge portions is provided proximate the distal tip end of the high-frequency electrode so as to be obliquely backward, the concavo-convex portion being provided at the obliquely backward side edge portion.

4. The high-frequency treating instrument according to claim 1, wherein at least one of the side edge portions proximate the distal tip end of the high frequency electrode is inwardly slanted towards a central axis of the flexible sheath, the concavo-convex portion being provided at the inwardly slanted side edge portion.

* * * * *